United States Patent [19]

Krass

[11] Patent Number: 4,584,403

[45] Date of Patent: Apr. 22, 1986

[54] HERBICIDALLY ACTIVE SUBSTITUTED DIPHENYL ETHER OXIME DERIVATIVES

[75] Inventor: Dennis K. Krass, Canal Fulton, Ohio

[73] Assignee: PPG Industries, Inc., Pittsburgh, Pa.

[21] Appl. No.: 584,181

[22] Filed: Feb. 27, 1984

Related U.S. Application Data

[63] Continuation-in-part of Ser. No. 484,095, Apr. 11, 1983.

[51] Int. Cl.$^4$ .......................................... C07C 131/00
[52] U.S. Cl. ..................................... 564/255; 71/125; 71/106; 564/259
[58] Field of Search .................. 160/21; 564/255, 259; 71/125, 106

[56] References Cited

U.S. PATENT DOCUMENTS 3,282,991 11/1961 Klein et al. .......................... 560/103

FOREIGN PATENT DOCUMENTS 2049695 12/1980 United Kingdom .................. 560/21

Primary Examiner—Paul J. Killos
Attorney, Agent, or Firm—Edward J. Whitfield

[57] ABSTRACT

This invention relates to certain herbicidally active substituted diphenyl ether oxime derivatives, herbicidal compositions of the same and the use thereof for pre-emergence and postemergence control of noxious plants, i.e., weeds.

4 Claims, No Drawings

HERBICIDALLY ACTIVE SUBSTITUTED DIPHENYL ETHER OXIME DERIVATIVES

CROSS-REFERENCE TO RELATED APPLICATION

This application is a continuation-in-part of application Ser. No. 484,095, filed Apr. 11, 1983.

FIELD OF THE INVENTION

This invention relates to certain substituted diphenyl ether oxime derivatives and to the use of same to control the growth of noxious plants, i.e., weeds.

DESCRIPTION OF THE INVENTION

This invention provides herbicidally active substituted diphenyl ether oxime compounds represented by the Formula I:

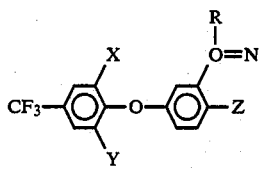

wherein:
X and Y are hydrogen or halogen provided that at least one of X or Y is halogen;
Z is nitro, halogen or cyano;
R is hydrogen, halogen, $C_1$ to $C_4$ alkyl or haloalkyl, $C_1$ to $C_3$ alkoxy or alkylthio, mono or dialkylamino; or cyano;
$R^1$ is hydrogen or $C_1$ to $C_3$ alkyl,
$R^2$ or $R^3$ are the same or different and represent hydrogen, $C_1$ to $C_3$ alkyl,

wherein $R^5$ is hydrogen, halogen, hydroxy, $C_1$ to $C_4$ alkyl or haloalkyl, $C_1$ to $C_3$ alkoxy, alkylthio alkylsulfonyl or alkylsulfinyl, amino, mono- or dialkyl amino, the alkyl portion of which may be halo substituted, cyano or nitro and m is 1, 2 or 3; or

form a ring structure containing 4 to 7 carbon atoms and which may contain up to 2 hetero atoms; and
n is 0, 1, 2, 3 or 4.

Suitable alkyl radicals of which the various 'R' groups are representative include methyl, ethyl, n-propyl, iso-propyl, n-butyl, t-butyl or iso-butyl. Chloromethyl, chloroethyl, bromomethyl, bromoethyl, trifluoromethyl and the like are exemplary haloalkyls. As examples of alkoxy and alkylthio radicals there may be mentioned methoxy, ethoxy, propoxy, thiomethyl, thioethyl or the like. Mono or dialkyl amino groups include methylamino, dimethylamino, methylethylamino, diethylamino or the like. Halogens represented by X, Y, Z and R include bromine, chlorine or fluorine, preferably bromine or chlorine.

Preferred compounds of the Formula I are those wherein X is halogen, e.g., chlorine; Y is hydrogen; and Z is nitro.

Compounds of the Formula I may be prepared using techniques known to and starting materials available to the art. For example, a Formula I compound may be prepared by reacting an appropriately substituted diphenylether oxime-O-alkanoyl halide of the Formula II:

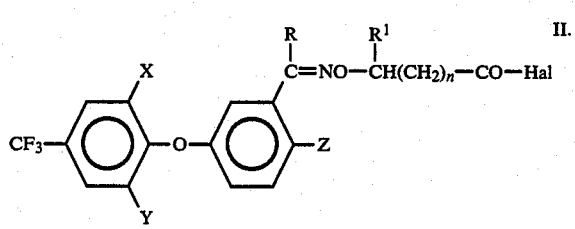

wherein X, Y, Z, R and $R^1$ are as previously defined and Hal is halogen, preferably bromine or chlorine, with an appropriately substituted oxime of the Formula III:

wherein $R^2$ and $R^3$ are as previously defined. The reaction is typically conducted in an inert solvent in the presence of an acid acceptor and at temperature ranging from ambient to reflux. The Formula II alkanoyl halide may readily be prepared by halogenating, i.e., chlorinating or brominating an appropriately substituted diphenylether oxime-O-alkanoic acid of the Formula IV:

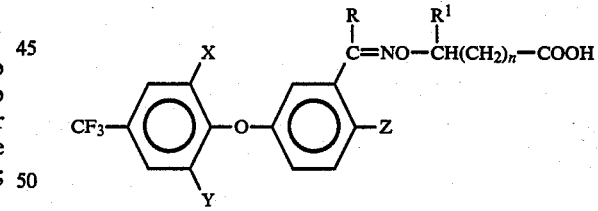

wherein X, Y, Z, R an $R^1$ are as previously defined. Certain of the Formula IV compounds are described, for example, in U.S. Pat. No. 4,344,789.

The following Example is illustrative of the preparation of a compound of this invention.

EXAMPLE

Preparation of O-[(isopropylideneaminooxy)carbonyl]methyl 5-(2-chloro-4-trifluoromethylphenoxy)-2-nitroacetophenone oxime.

(a) A 50 milliliter flask was charged with 4.32 grams (0.01 mole) of 5-(2-chloro-4-trifluoromethylphenoxy)-2-nitroacetophenone oxime-O-acetic acid and 20 milliliters of dry carbon tetrachloride. To this stirred mixture was added 2.36 grams (0.02 mole) of thionyl chloride and 2 drops of dimethylformamide. A condenser and drying tube were attached to the flask and the reaction mixture was heated to reflux. After about 5 hours refluxing, excess thionyl chloride and solvent were stripped under aspirator vacuum to a total volume of about 5 milliliters, the pot temperature being maintained below 30° C. This residue, identified as 5-(2-chloro-4-trifluoromethylphenoxy)-2-nitroacetophenone oxime-O-acetyl chloride, was diluted, with dry carbon tetrachloride, to a total volume of 25 milliliters.

(b) A 12.5 milliliter aliquot of the above carbon tetrachloride solution was added dropwise, over an 18 minute period, to a solution of 0.4 gram (0.0055 mole) of acetone oxime in 10 milliliters of dry carbon tetrachloride containing 0.56 gram (0.055 mole) of triethylamine. A precipitate formed almost immediately on addition of acid chloride and the reaction was observed to be mildly exothermic, the temperature having risen from ambient to 37° C. over the addition period. The reaction mixture was stirred at ambient temperature of about 18 hours after which stirring was discontinued and the reaction mixture was allowed to stand quiescent for about 2 days at ambient temperature. The reaction mixture was then filtered and the precipitate was washed with carbon tetrachloride. The filtrate was washed twice with 50 milliliter portions of water and dried over anhydrous magnesium sulfate. Filtration and removal of solvent afforded 2.58 grams of a brown oil. NMR and MS analyses confirmed the product to be O-[isopropylideneaminooxy)carbonyl]methyl 5-(2-chloro-4-trifluoromethylphenoxy)-2-nitroacetophenone oxime.

Although the invention has been illustrated by the foregoing Example with regard to the preparation of a specific compound within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil before emergence of weeds therefrom or to the leaf surface after emergence from the soil, a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extent of weed infestation, climatic conditions, solid conditions, method of application, and the like. Typically, as little as one or less pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.25 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America* may be used in combination with a compound or compounds of the invention and related herbicides. Typically such formulations will contain from about 5 to about 95 percent by weight of a compound of this invention.

The herbicidal formulations contemplated herein can be applied by any of several methods known to the art. Generally, the formulation will be surface applied as an aqueous spray. Such application can be carried out by conventional ground equipment, of if desired, the sprays can be aerially supplied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for preemergence or postemergence control of a wide variety of broadleaf and grassy weeds. Typical of the various species of vegetative growth that may be controlled or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horetail ironweed, sesbania, cattail, wintercress, horsenettle, nutsedge, milkweed, sicklepod, and the like.

The compound prepared as described in the Example was tested for herbicidal efficacy, against a variety of broadleaf and grassy weed species, under controlled laboratory conditions of light, humidity and temperature. Solvent solutions of the compound were applied, both preemergence and postemergence, to test flats containing the various weed species, and herbicidal efficacy was determined by visual inspection, periodically after application of the compounds. Herbicidal efficacy was determined on a scale of from 0 (no injury) to 10 (all plants dead). More particularly, the compound of the Example was found effective at a rate of application of 1.0 pound per acre in preemergence control of teaweed, jimsonweed, coffeeweed, velvetleaf, tall morningglory, yellow foxtail, large crabgrass, and Johnsongrass, herbicidal injury ratings ranging from 7 to 10 having been observed up to 21 days subsequent to application.

At a postemergence rate of application of 1.0 pound per acre, the compound of the Example was found effective, particularly against broadleaved weeds, i.e., teaweed, jimsonweed, wild mustard, coffeeweed, velvetleaf and tall morningglory, herbicidal injury ratings of from 8 to 10 having been observed up to 21 days subsequent to application.

Although the invention has been described in considerable detail by the foregoing, it is to be understood that many variations may be made therein by those skilled in the art without departing from the spirit and scope thereof as defined by the appended claims.

I claim:

1. A compound represented by the formula:

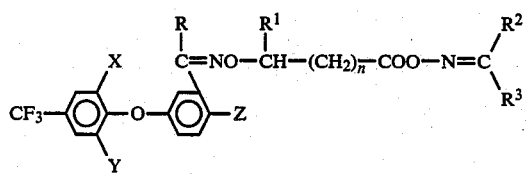

wherein:

X and Y are hydrogen or halogen provided that at least one of X or Y is halogen;

Z is nitro, halogen or cyano;

R is hydrogen, halogen, $C_1$ to $C_4$ alkyl or haloalkyl, $C_1$ to $C_3$ alkoxy or alkylthio, mono or dialkylamino; or cyano;

$R^1$ is hydrogen or $C_1$ to $C_3$ alkyl, $R^2$ or $R^3$ are the same or different and represent hydrogen, $C_1$ to $C_3$ alkyl,

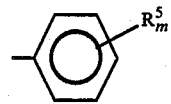

wherein $R^5$ is hydrogen, halogen, hydroxy, $C_1$ to $C_4$ alkyl or haloalkyl, $C_1$ to $C_3$ alkoxy, alkylthio alkylsulfonyl or alkylsulfinyl, amino, mono- or dialkyl amino, the alkyl portion of which may be halo substituted, cyano or nitro and m is 1, 2 or 3; or

form a ring structure containing 4 to 7 carbon atoms and which may contain up to 2 hetero atoms; and n is 0, 1, 2, 3 or 4.

2. A compound of claim 1 that is O-[(isopropylideneaminooxy)carbonyl]methyl 5-(2-chloro-4-trifluoromethylphenoxy)-2-nitroacetophenone-oxime.

3. A herbicidal composition containing an inert carrier and a herbicidally effective amount of a compound or mixture of compounds defined in claim 1.

4. In a method of controlling weeds wherein a herbicidally effective amount of herbicide is applied to a growth medium prior to emergence of the weeds therefrom or the weeds subsequent to their emergence from the growth medium, wherein the improvement resides in using as the herbicide a compound or mixture of compounds defined by claim 1.

* * * * *